United States Patent [19]

Heinemann et al.

[11] Patent Number: 5,061,312

[45] Date of Patent: Oct. 29, 1991

[54] FUNGICIDAL N-VINYL-3-CYANO-4-PHENYL-PYRROLES

[75] Inventors: Ulrich Heinemann, Leichlingen; Detlef Wollweber, Wuppertal; Wilhelm Brandes, Leichlingen; Stefan Dutzmann, Duesseldorf; Gerd Hänssler, Leverkusen, all of Fed. Rep. of Germany

[73] Assignee: Bayer Aktiengesellschaft, Leverkusen, Fed. Rep. of Germany

[21] Appl. No.: 539,631

[22] Filed: Jun. 18, 1990

[30] Foreign Application Priority Data

Jul. 5, 1989 [DE] Fed. Rep. of Germany .... 3922104.0

[51] Int. Cl.$^5$ .................. C07D 207/34; C07D 403/06; C07D 401/06; A01N 43/36
[52] U.S. Cl. ......................... 71/95; 540/602; 546/281; 548/524; 548/526; 548/561; 71/88; 71/94
[58] Field of Search ...................... 548/526, 561, 524; 71/95, 88.94; 546/281; 540/602

[56] References Cited

FOREIGN PATENT DOCUMENTS

| 130149 | 6/1984 | European Pat. Off. . |
|---|---|---|
| 0133247 | 2/1985 | European Pat. Off. . |
| 182737 | 5/1986 | European Pat. Off. . |
| 0182737 | 5/1986 | European Pat. Off. . |
| 206999 | 6/1986 | European Pat. Off. . |
| 0206999 | 12/1986 | European Pat. Off. . |
| 236272 | 2/1987 | European Pat. Off. . |
| 0281731 | 9/1988 | European Pat. Off. . |
| 0310558 | 4/1989 | European Pat. Off. . |
| 3718375 | 12/1988 | Fed. Rep. of Germany . |
| 2141709 | 1/1985 | United Kingdom . |

Primary Examiner—Mark L. Berch
Attorney, Agent, or Firm—Sprung, Horn, Kramer & Woods

[57] ABSTRACT

Fungicidal N-vinyl-3-cyano-4-phenyl-pyrroles of the formula

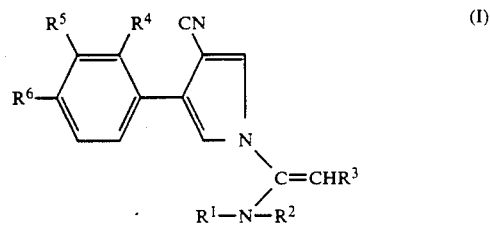

in which
$R^1$ represents alkyl,
$R^2$ represents alkyl, or
$R^1$ and $R^2$ together with the nitrogen atom to which they are bonded form a 5- to 7-membered, saturated ring which is optionally monosubstituted to polysubstituted by identical or different substituents,
$R^3$ represents alkyl,
$R^4$ represents hydrogen, halogen, alkyl, halogenoalkyl, alkoxy, halogenoalkoxy, alkylthio or halogenoalkylthio,
$R^5$ represents hydrogen, halogen, alkyl, halogenoalkyl, alkoxy, halogenoalkoxy, alkylthio or halogenoalkylthio, or
$R^4$ and $R^5$ together represent halogen-substituted alkylenedioxy, and
$R^6$ represents hydrogen or halogen.

12 Claims, No Drawings

FUNGICIDAL N-VINYL-3-CYANO-4-PHENYL-PYRROLES

The invention relates to new N-vinyl-3-cyano-4-phenyl-pyrrole derivatives, to a process for their preparation, and to their use for combating pests, in particular phytopathogenic fungi.

It is known that 3-cyano-4-phenyl-pyrrole derivatives which are unsubstituted or substituted on the pyrrole nitrogen have, for example, a fungicidal activity (cf, for example, European Patent 130,149, European Patent 182,737, European Patent 206,999, European Patent 236,272, GB 2,141,709, DE 3,718,375). For example, European Patent 182,737 describes compounds which are substituted on the pyrrole nitrogen, for example N-vinyl-3-cyano-4-(2,3-dichlorophenyl)-pyrrole, which have fungicidal properties.

However, the activity of this previously known compound is not entirely satisfactory in all fields of application, in particular when low application rates and concentrations are used.

New N-vinyl-3-cyano-4-phenyl-pyrrole derivatives have been found, of the general formula (I)

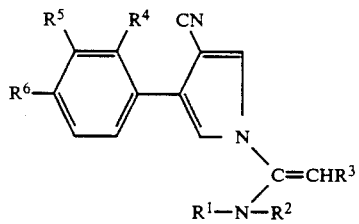

in which
- $R^1$ represents alkyl,
- $R^2$ represents alkyl, or
- $R^1$ and $R^2$ together with the nitrogen atom to which they are bonded form a 5- to 7-membered, saturated ring which is optionally monosubstituted to polysubstituted by identical or different substituents,
- $R^3$ represents alkyl,
- $R^4$ represents hydrogen, halogen, alkyl, halogenoalkyl, alkoxy, halogenoalkoxy, alkylthio or halogenoalkylthio,
- $R^5$ represents hydrogen, halogen, alkyl, halogenoalkyl, alkoxy, halogenoalkoxy, alkylthio or halogenoalkylthio, or
- $R^4$ and $R^5$ together represent halogen-substituted alkylenedioxy, and
- $R^6$ represents hydrogen or halogen.

Furthermore, it has been found that the new N-vinyl-3-cyano-4-phenyl-pyrrole derivatives of the general formula (I)

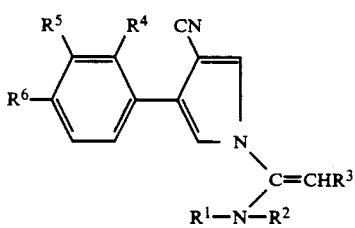

in which

- $R^1$ represents alkyl,
- $R^2$ represents alkyl, or
- $R^1$ and $R^2$ together with the nitrogen atom to which they are bonded form a 5- to 7-membered, saturated ring which is optionally monosubstituted to polysubstituted by identical or different substituents,
- $R^3$ represents alkyl,
- $R^4$ represents hydrogen, halogen, alkyl, halogenoalkyl alkoxy, halogenoalkoxy, alkylthio or halogenoalkylthio,
- $R^5$ represents hydrogen, halogen, alkyl, halogenoalkyl, alkoxy, halogenoalkoxy, alkylthio or halogenoalkylthio, or
- $R^4$ and $R^5$ together represent halogen-substituted alkylenedioxy, and
- $R^6$ represents hydrogen or halogen, are obtained when 3-cyano-4-phenyl-pyrrole derivatives of the formula (II)

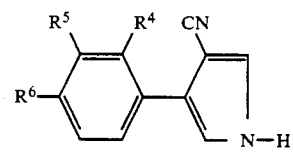

in which
$R^4$, $R^5$ and $R^6$ have the abovementioned meanings, are reacted with 1-aminoacetylene derivatives of the formula (III)

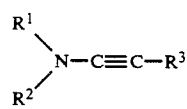

in which
$R^1$, $R^2$ and $R^3$ have the abovementioned meanings, if appropriate in the presence of a diluent.

Finally, it has been found that the new N-vinyl-3-cyano-4-phenyl-pyrrole derivatives of the general formula (I) have a good action against pests.

Preferred radicals listed in the formulae mentioned hereinabove and hereinafter are explained below:

Alkyl in the general formulae preferably denotes straight-chain or branched alkyl having 1 to 6 carbon atoms, preferably having 1 to 4 and particularly preferably having 1 or 2 carbon atoms; methyl, ethyl, n- and i-propyl and n-, i-, s- and t-butyl may be mentioned by way of example.

Alkoxy as a substituent preferably represents straight-chain or branched alkoxy having 1 to 6, particularly preferably 1 to 4, carbon atoms per alkyl radical; the following may be mentioned by way of example: methoxy, ethoxy, n- or i-propoxy and n-, i-, s- and t-butoxy.

Halogenoalkyl and halogenoalkoxy as substituents preferably represent straight-chain or branched radicals having in each case 1 to 4 carbon atoms, particularly preferably having 1 or 2 carbon atoms and in each case 1 to 9 or 1 to 5 identical or different halogen atoms, as defined under halogen; the following may be mentioned by way of example: fluoromethyl, chloromethyl, bromomethyl, fluoroethyl, chloroethyl, bromoethyl, fluoro-n-propyl, chloro-n-propyl, difluoromethyl, trifluoromethyl, dichloromethyl, trichloromethyl, difluoroethyl, trifluoroethyl, trichloroethyl, chlorodifluoromethyl, trifluorochloroethyl, chlorobutyl, fluorobutyl, fluoromethoxy, chloromethoxy, bromomethoxy, fluoroethoxy, chloroethoxy, bromoethoxy, fluoropropoxy, chloropropoxy, bromopropoxy, fluorobutoxy, chlorobutoxy, fluoro-i-propoxy, chloro-i-propoxy, difluoromethoxy, trifluoromethoxy, dichloromethoxy, trichloromethoxy, difluoroethoxy, trifluoroethoxy, tetrafluoroethoxy, trichloroethoxy, chlorodifluoromethoxy or trifluorochloroethoxy, with particular emphasis on trifluoromethyl and trifluoromethoxy.

Halogenoalkylthio as a substituent in the radicals preferably represents straight-chain or branched radicals having in each case 1 to 4 carbon atoms, particularly preferably having 1 or 2 carbon atoms and in each case 1 to 9 or 1 to 5 identical or different halogen atoms, as defined under halogen; the following may be mentioned by way of example: fluoromethylthio, chloromethylthio, bromomethylthio, fluoroethylthio, chloroethylthio, bromoethylthio, fluoropropylthio, chloropropylthio, bromopropylthio, fluorobutylthio, chlorobutylthio, bromobutylthio, fluoro-i-propylthio, chloro-i-propylthio, difluoromethylthio, trifluoromethylthio, dichloromethylthio, trichloromethylthio, difluoroethylthio, trifluoroethylthio, tetrafluoroethylthio, trichloroethylthio, chlorodifluoromethylthio and trifluorochloroethylthio.

Halogen as such or in the definitions of halogenoalkyl, halogenoalkoxy and halogenoalkylthio represents fluorine, chlorine, bromine and/or iodine, particularly fluorine, chlorine and/or bromine, and, in particular, fluorine or chlorine.

Alkylthio as a substituent preferably represents straight-chain or branched alkylthio, preferably having 1 to 6 carbon atoms, examples of meanings being the following groups: methylthio-, ethylthio-, propylthio-, butylthio-, pentylthio as well as their isomers, such as, for example, i-propylthio, i-, s- and t-butylthio, 1-methyl-butylthio, 2-methyl-butylthio- and 3-mathylbutylthio. Preferred alkylthio radicals contain 1 to 4 carbon atoms. Methylthio, ethylthio, n-, i- and s-propylthio and n-, i-, s- and t-butylthio are particularly preferred.

Formula (I) provides a general definition of the N-vinyl-3-cyano-4-phenyl-pyrrole derivatives according to the invention.

Preferred compounds of the formula (I) are those in which $R^1$ represents a straight-chain or branched alkyl having 1 to 4 carbon atoms, $R^2$ represents a straight-chain or branched alkyl having 1 to 4 carbon atoms, or $R^1$ and $R^2$ together with the nitrogen atom to which they are bonded form a 5- to 7-membered saturated ring which is optionally monosubstituted to pentasubstituted by identical or different substituents from the series comprising halogen, alkyl having 1 to 4 carbon atoms, alkoxy having 1 to 4 carbon atoms, or halogenoalkyl or halogenoalkoxy, each of which has 1 to 4 carbon atoms and 1 to 9 identical or different halogen atoms, $R^3$ represents a straight-chain or branched alkyl having 1 to 4 carbon atoms, $R^4$ represents hydrogen, halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, straight-chain or branched alkylthio having 1 to 4 carbon atoms, or straight-chain or branched halogenoalkylthio having 1 to 4 carbon atoms and 1 to 9 identical or different halogen atoms, $R^5$ represents hydrogen, halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, or straight-chain or branched halogenoalkylthio having 1 to 4 carbon atoms and 1 to 9 identical or different halogen atoms, or $R^4$ and $R^5$ together represent methylenedioxy which is monosubstituted or disubstituted by fluorine, and $R^6$ represents hydrogen or fluorine.

Particularly preferred compounds of the formula (I) are those in which $R^1$ represents methyl, ethyl, n or i-propyl or n-butyl, $R^2$ represents methyl, ethyl, n or i-propyl or n-butyl, or $R^1$ and $R^2$ together with the nitrogen atom to which they are bonded form a 5- to 7-membered saturated ring, $R^3$ represents methyl or ethyl, $R^4$ represents hydrogen, fluorine, chlorine, bromine, methyl, ethyl, halogenoalkyl having 1 or 2 carbon atoms and 1 to 5 identical or different halogen atoms, in particular fluorine and/or chlorine atoms, methoxy, ethoxy, halogenoalkoxy having 1 or 2 carbon atoms and 1 to 5 identical or different halogen atoms, in particular fluorine and/or chlorine atoms, methylthio, ethylthio, halogenoalkylthio having 1 or 2 carbon atoms and 1 to 5 identical or different halogen atoms, in particular fluorine or chlorine atoms, $R^5$ represents hydrogen, fluorine, chlorine, bromine, methyl, ethyl, halogenoalkyl having 1 or 2 carbon atoms and 1 to 5 identical or different halogen atoms, in particular fluorine and/or chlorine atoms, methoxy, ethoxy, halogenoalkoxy having 1 or 2 carbon atoms and 1 to 5 identical or different halogen atoms, in particular fluorine and/or chlorine atoms, methylthio, ethylthio, halogenoalkylthio having 1 or 2 carbon atoms and 1 to 5 identical or different halogen atoms, in particular fluorine or chlorine atoms, or $R^4$ and $R^5$ together represent methylenedioxy which is disubstituted by fluorine, and $R^6$ represents hydrogen or fluorine.

Very particularly preferred compounds of the formula (I) are those in which $R^1$ represents methyl or ethyl, $R^2$ represents methyl or ethyl, $R^3$ represents methyl or ethyl, $R^4$ represents hydrogen, fluorine, chlorine, methyl, ethyl or trifluoromethyl, $R^5$ represents hydrogen, chlorine, methyl or trifluoromethyl, and $R^6$ represents hydrogen or fluorine.

The preferred definitions given for the compounds of the formula (I) are also true for the starting compounds of the formula (II) and of the formula (III).

The following N-vinyl-3-cyano-4-phenyl-pyrrole derivatives of the general formula (I)

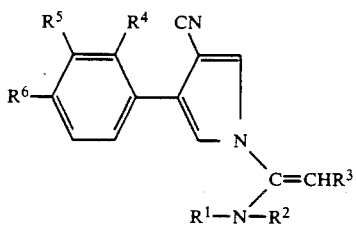

may be mentioned individually in addition to the compounds mentioned in the Preparation Examples:

TABLE 1

| $R^1$ | $R^2$ | $R^3$ | $R^4$ | $R^5$ | $R^6$ |
|---|---|---|---|---|---|
| —$CH_3$ | —$CH_3$ | —$CH_3$ | F | Cl | H |
| —$C_2H_5$ | —$CH_3$ | —$C_2H_5$ | F | Cl | H |
| —$C_3H_7$-n | —$C_2H_5$ | —$CH_3$ | F | Cl | H |
| —$C_3H_7$-i | —$CH_3$ | —$CH_3$ | F | Cl | H |
| —$C_4H_9$-n | —$C_3H_7$-i | —$CH_3$ | F | Cl | H |
| —$CH_3$ | —$C_3H_7$-i | —$C_2H_5$ | F | Cl | H |
| —$CH_3$ | $C_2H_5$ | —$CH_3$ | Cl | Cl | H |
| —$C_2H_5$ | —$C_3H_7$-n | —$C_2H_5$ | Cl | Cl | H |
| —$C_2H_5$ | —$C_2H_5$ | —$CH_3$ | F | Cl | F |
| —$CH_3$ | —$C_3H_7$-i | —$CH_3$ | F | Cl | F |
| —$C_2H_5$ | —$C_4H_9$-n | —$CH_3$ | Cl | Cl | F |
| —$C_2H_5$ | —$C_2H_5$ | —$CH_3$ | —$CH_3$ | —$CF_3$ | H |
| —$CH_3$ | —$C_3H_7$-i | —$CH_3$ | —$CH_3$ | —$CF_3$ | H |
| —$C_3H_7$-n | —$C_2H_5$ | —$CH_3$ | —$CH_3$ | —$CF_3$ | H |
| —$C_2H_5$ | —$CH_3$ | —$CH_3$ | —$CH_3$ | —$CH_3$ | H |
| —$CH_3$ | —$CH_3$ | —$C_2H_5$ | Cl | Cl | F |
| —$C_2H_5$ | —$C_2H_5$ | —$C_2H_5$ | —$CH_3$ | Cl | H |
| —$C_2H_5$ | —$C_3H_7$-n | —$CH_3$ | —O—$CF_2$—O— | | H |
| —$CH_3$ | —$C_3H_7$-n | —$CH_3$ | —O—$CF_2$—O— | | H |
| —$C_2H_5$ | —$CH_3$ | —$CH_3$ | —O—$CF_2$—O— | | F |
| —$C_2H_5$ | —$CH_3$ | —$CH_3$ | —$CH_3$ | —$OCF_3$ | H |
| —$C_2H_5$ | —$C_2H_5$ | —$CH_3$ | —$CH_3$ | —$SCH_3$ | H |
| —$C_2H_5$ | —$C_2H_5$ | —$CH_3$ | Cl | —$OCF_3$ | H |
| —$C_2H_5$ | —$C_3H_7$-i | —$CH_3$ | —$CH_3$ | —$OCH_3$ | H |
| —$C_2H_5$ | —$CH_3$ | —$CH_3$ | F | —$OCH_3$ | F |
| —$C_2H_5$ | —$C_3H_7$-i | —$CH_3$ | —$CH_3$ | —$SCH_3$ | H |
| —$C_2H_5$ | —$CH_3$ | —$CH_3$ | F | Br | H |
| —$C_4H_9$-i | —$C_2H_5$ | —$CH_3$ | F | Br | F |
| —$C_3H_7$-i | —$C_2H_5$ | —$CH_3$ | Br | Br | H |
| —$C_4H_9$-n | —$C_2H_5$ | —$CH_3$ | F | Br | F |
| —$CH_3$ | —$C_2H_5$ | —$C_2H_5$ | Br | Br | F |
| —$(CH_2)_4$— | | —$CH_3$ | F | Cl | H |
| —$(CH_2)_4$— | | —$CH_3$ | F | Cl | F |
| —$(CH_2)_5$— | | —$CH_3$ | Cl | Cl | H |
| —$(CH_2)_5$— | | —$CH_3$ | F | Cl | H |
| —$(CH_2)_5$— | | —$C_2H_5$ | $CH_3$ | $CF_3$ | H |
| —$(CH_2)_6$— | | —$CH_3$ | Cl | Cl | H |

If, for example, 3-cyano-4-(2-fluoro-3-chlorophenyl)-pyrrole and 1-diethylaminopropine are used as starting substances, the course of the reaction of the process according to the invention may be represented by the following equation:

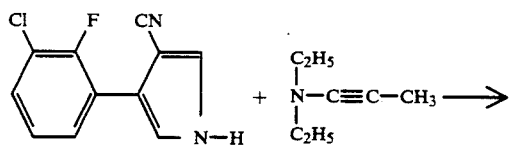

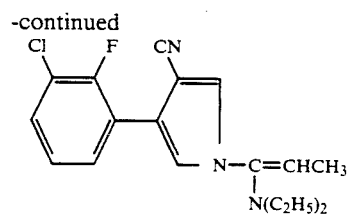

Formula (II) provides a general definition of the substituted 3-cyano-4-phenyl-pyrrole derivatives starting substances for carrying out the process according to the invention. In this formula (II), $R^4$, $R^5$ and $R^6$ represent those radicals which have already been mentioned for these substituents in connection with the description of the substances of the formula (I) according to the invention.

Some of the substituted 3-cyano-4-phenyl-pyrrole derivatives of the formula (II) are known.

For example, European Patent 206,999 describes the preparation of 3-(2,2-difluorobenzodioxol-4-yl)-4-cyano-pyrrole, U.S. Pat. No. 4,778,901 and European Patent 174,910 describe the preparation of 3-cyano-4-phenyl-pyrroles which are unsubstituted in the phenyl ring or substituted by halogen, alkyl or halogenoalkyl, and preparation processes are described in DE 3,718,375, DE 3,737,984 and DE 3,718,375 inter alia.

Formula (III) provides a general definition of the 1-aminoacetylene derivatives to be used as starting substances in the process according to the invention for the preparation of compounds of the formula (I).

$R^1$, $R^2$ and $R^3$ in formula (III) have those meanings which have already been described above for $R^1$, $R^2$ and $R^3$ in connection with the description of the compounds of the formula (I) according to the invention.

The 1-aminoacetylene derivatives are known compounds of organic chemistry and/or can be prepared by processes which are known per se (cf. Studies in Organic Chemistry, Preparative Acetylenic Chemistry Vol. 34 (2nd Edition), Elsevier 1988, p. 235).

Suitable diluents for carrying out the process according to the invention are inert organic solvents. These include, in particular, aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran, or ethylene glycol dimethyl ether or ethylene glycol diethyl ether, amides, such as dimethylformamide, dimethylacetamide, N-methylformanilide, N-methylpyrrolidone or hexamethylphosphoric triamide, or sulphoxides, such as dimethyl sulphoxide.

The reaction temperatures in the process according to the invention can be varied within a substantial range. In general, the process is carried out at temperatures of between −40° C. and +120° C., preferably at temperatures of between 0° C. and +60° C.

For carrying out the process according to the invention, 1.0 to 2.0 moles, preferably 1.0 to 1.2 moles, of 1-aninoacetylene derivative of the formula (III) are generally employed per mole of 3-cyano-4-phenyl-pyrrole derivative of the formula (II).

The reaction is carried out and the reaction products are worked up and isolated by generally customary methods.

The active compounds according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Pythium species, such as, for example, *Pythium ultimum;*
Phytophthora species, such as, for example, *Phytophthora infestans;*
Pseudoperonospora species, such as, for example, *Pseudoperonospora humuli* or *Pseudoperonospora cubensis;*
Plasmopara species, such as, for example, *Plasmopara viticola;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: *Drechslera,* syn: *Helminthosporium*);
Cochliobolus species, such as, for example, *Cochliobolus sativus* (conidia form: *Drechslera,* syn: *Helminthosporium*);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae* and
Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In this connection, the active compounds according to the invention can be employed with particularly good success for combating diseases in fruit and vegetable growing, such as, for example, against the pathogen causing grey mould of beans (*Botrytis cinerea*), or for combating rice diseases, such as, for example, against the pathogen causing rice blast disease (*Pyricularia oryzae*), or against *Erysiphe graminis* and against *Pyrenophora teres* in barley.

Furthermore, some of the active compounds according to the invention also show fungicidal actions against Leptosphaeria and Fusarium in cereal crops. In addition, some of the active compounds according to the invention also have a good and broad in-vitro action.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, and ULV cold mist and warm mist formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene, or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant those liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates; arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% of, are required at the place of action.

PREPARATION EXAMPLES

Example 1

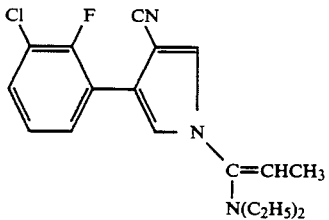

0.9 g (4 mmol) of 3-cyano-4-(2-fluoro-3-chlorophenyl)-pyrrole and 0.5 g (4.5 mmol) of 1-diethylaminopropine are dissolved in 20 ml of dry dichloromethane, and the solution is stirred for 12 hours at room temperature. The solvent and excess 1-diethylaminopropine are subsequently removed completely in vacuo. This gives 1.4 g (100% of theory) of N-(1-diethylamino-2-methylvinyl)-3-cyano-4-(2-fluoro-3-chlorophenyl)-pyrrole as an oil of refractive index $n_D^{20} = 1.5550$.

The compounds of the formula (I)

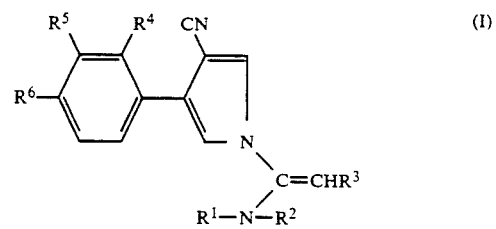

listed in the table below can be prepared analogously to Example 1:

| Example No. | $R^1$ | $R^2$ | $R^3$ | $R^4$ | $R^5$ | $R^6$ | Physical data |
| --- | --- | --- | --- | --- | --- | --- | --- |
| 2 | —$C_2H_5$ | —$C_2H_5$ | —$CH_3$ | Cl | Cl | H | $n_D^{20}$ = 1.5802 |
| 3 | —$C_2H_5$ | —$C_2H_5$ | —$CH_3$ | F | Cl | F | mp 92° C. |
| 4 | —$C_2H_5$ | —$C_2H_5$ | —$CH_3$ | —$CH_3$ | —$CF_3$ | H | Oil |
| 5 | —$CH_3$ | —$CH_3$ | —$CH_3$ | F | Cl | H | Oil |
| 6 | —$CH_3$ | —$CH_3$ | —$CH_3$ | Cl | Cl | H | Oil |
| 7 | —$CH_3$ | —$CH_3$ | —$CH_3$ | F | Cl | F | Oil |
| 8 | —$C_2H_5$ | —$C_2H_5$ | —$CH_3$ | Cl | Cl | Cl | m.p. 116° C. |

USE EXAMPLES

Example A

Erysiphe test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of mildew pustules.

Evaluation is carried out 7 days after the inoculation.

In this test, a very good activity of a degree of effectiveness of 88% is shown, at an active compound concentration of 0.025% by weight, for example by the compound of Preparation Example 2.

Example B

Pyrenophora teres test (barley)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried, the plants are sprayed with a conidia suspension of *Pyrenophora teres*. The plants then remain in an incubation cabin at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a good activity is shown, at an active compound concentration of 0.025% by weight, for example by the compound of Preparation Example 2.

Example C

Pyricularia test (rice)/protective
Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the preparation of active compound until dripping wet. After the spray coating has dried, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a good activity is shown, at an active compound concentration of 0.025% by weight in the spray liquor, for example by the compounds of the Preparation Examples 1 and 2.

Example D

Botrytis test (dwarf beans)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humid chamber at 20° C. 3 days after the inoculation, the size of the infected spots on the leaves is evaluated.

In this test, a good activity is shown, at an active compound concentration of 100 ppm, for example by the compounds of Preparation Examples 1 and 2.

It is understood that the specification and examples are illustrative but not limitative of the present invention and that other embodiments within the spirit and scope of the invention will suggest themselves to those skilled in the art.

We claim:

1. An N-vinyl-3-cyano-4-phenyl-pyrrole of the formula

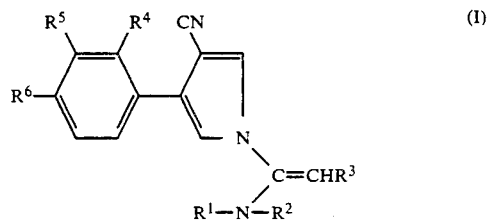

in which
$R^1$ represents alkyl,
$R^2$ represents alkyl, or
$R^1$ and $R^2$ together with the nitrogen atom to which they are bonded form a 5- to 7-membered, saturated monoaza polymethylene ring which is optionally monosubstituted to polysubstituted by identical or different substituents, selected from the group consisting of halogen, alkyl having 1 to 4 carbon atoms, alkoxy having 1 to 4 carbon atoms, and halogenoalkyl or halogenoalkoxy, each of which has 1 to 4 carbon atoms and 1 to 9 identical or different halogen atoms,
$R^3$ represents alkyl,
$R^4$ represents hydrogen, halogen, alkyl, halogenoalkyl, alkoxy, halogenoalkoxy, alkylthio or halogenoalkylthio,
$R^5$ represents hydrogen, halogen, alkyl, halogenoalkyl, alkoxy, halogenoalkoxy, alkylthio or halogenoalkylthio, or
$R^4$ and $R^5$ together represent halogen-substituted alkylenedioxy, and
$R^6$ represents hydrogen or halogen.

2. An N-vinyl-3-cyano-4-phenyl-pyrrole according to claim 1,
in which
$R^1$ represents a straight-chain or branched alkyl having 1 to 4 carbon atoms,
$R^2$ represents a straight-chain or branched alkyl having 1 to 4 carbon atoms, or
$R^1$ and $R^2$ together with the nitrogen atom to which they are bonded form a 5- to 7-membered saturated monoaza polymethylene ring which is optionally monosubstituted to pentasubstituted by identical or different substituents selected from the group consisting of halogen, alkyl having 1 to 4 carbon atoms, alkoxy having 1 to 4 carbon atoms, and halogenoalkyl or halogenoalkoxy, each of which has 1 to 4 carbon atoms and 1 to 9 identical or different halogen atoms,
$R^3$ represents a straight-chain or branched alkyl having 1 to 4 carbon atoms;
$R^4$ represents hydrogen, halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, straight-chain or branched alkylthio having 1 to 4 carbon atoms, or straight-chain or branched halogenoalkylthio having 1 to 4 carbon atoms and 1 to 9 identical or different halogen atoms,
$R^5$ represents hydrogen, halogen, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy having 1 to 4 carbon atoms, straight-chain or branched halogenoalkoxy having 1 to 4 carbon atoms and 1 to 9 identical or different halogen atoms, or straight-chain or branched halogenoalkylthio having 1 to 4 carbon atoms and 1 to 9 identical different halogen atoms, or $R^4$ and $R^5$ together represent methylenedioxy which is monosubstituted or disubstituted by fluorine, and $R^6$ represents hydrogen or fluorine.

3. An N-vinyl-3-cyano-4-phenyl-pyrrole according to claim 1, in which $R^1$ represents methyl, ethyl, n- or iso-propyl or n-butyl, $R^2$ represents methyl, ethyl, n- or iso-propyl or n-butyl, or $R^1$ and $R^2$ together with the nitrogen atom to which they are bonded represent a 5- to 7-membered saturated monoaza polymethylene unsubstituted ring, $R^3$ represents methyl or ethyl, $R^4$ represents hydrogen, fluorine, chlorine, bromine, methyl, ethyl, halogenoalkyl having 1 or 2 carbon atoms and 1 to 5 identical or different halogen atoms, methoxy, ethoxy, halogenoalkoxy having 1 or 2 carbon atoms and 1 to 5 identical or different halogen atoms, methylthio, ethylthio or halogenoalkylthio having 1 or 2 carbon atoms and 1 to 5 identical or different halogen atoms, $R^5$ represents hydrogen, fluorine, chlorine, bromine, methyl, ethyl, halogenoalkyl having 1 or 2 carbon atoms and 1 to 5 identical or different halogen atoms, methoxy, ethoxy, halogenoalkoxy having 1 or 2 carbon atoms and 1 to 5 identical or different halogen atoms, methylthio, ethylthio or halogenoalkylthio having 1 or 2 carbon atoms and 1 to 5 identical or different halogen atoms, or $R^4$ and $R^5$ together represent methylenedioxy which is disubstituted by fluorine, and $R^6$ represents hydrogen or fluorine.

4. An N-vinyl-3-cyano-4-phenyl-pyrrole according to claim 1, in which $R^1$ represents methyl or ethyl, $R^2$ represents methyl or ethyl, $R^3$ represents methyl or ethyl, $R^4$ represents hydrogen, fluorine, chlorine, methyl, ethyl or trifluoromethyl, $R^5$ represents hydrogen, chlorine, methyl or trifluoromethyl, and $R^6$ represents hydrogen or fluorine.

5. A compound according to claim 1, wherein such compound is N-(1-diethylamino-2-methyl-vinyl)-3-cyano-4-(2-fluoro-3-chlorophenyl)-pyrrole of the formula

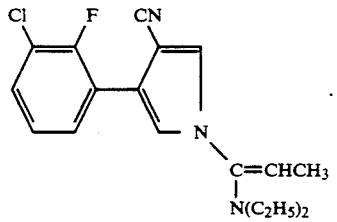

6. A compound according to claim 1, wherein such compound is N-(1-diethylamino-2-methyl-vinyl)-3-cyano-4-(2,3-dichlorophenyl)-pyrrole of the formula

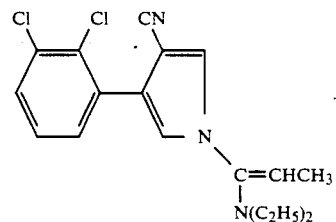

7. A compound according to claim 1, wherein such compound is N-(1-diethylamino-2-methyl-vinyl)-3-cyano-4-(2,4-difluoro-3-chlorophenyl)-pyrrole of the formula

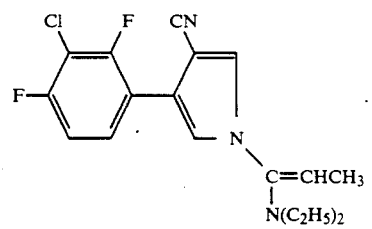

8. A compound according to claim 1, wherein such compound is N-(1-diethylamino-2-methyl-vinyl)-3-cyano-4-(2-methyl-3-trifluoromethyl)-pyrrole of the formula

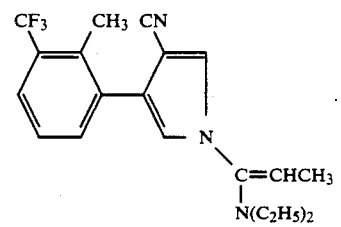

9. A compound according to claim 1, wherein such compound is N-(1-diethylamino-2-methyl-vinyl)-3-cyano-4-(2,3,4-trichloro)-pyrrole of the formula

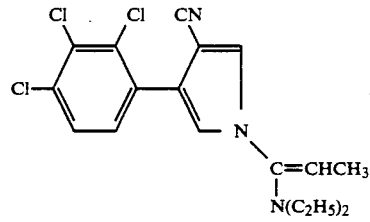

10. A fungicidal composition comprising a fungicidally effective amount of a compound according to claim 1 and an agriculturally acceptable diluent.

11. The method of combating fungi which comprises applying to such fungi or to a fungus habitat a fungicidally effective amount of a compound according to claim 1.

12. The method according to claim 11, wherein such compound is

N-(1-diethylamino-2-methyl-vinyl)-3-cyano-4-(2-fluoro-3-chlorophenyl)-pyrrole,

N-(1-diethylamino-2-methyl-vinyl)-3-cyano-4-(2,3-dichlorophenyl)-pyrrole,

N-(1-diethylamino-2-methyl-vinyl)-3-cyano-4-(2,4-difluoro-3-chlorophenyl)-pyrrole, N-(1-diethylamino-2-methyl-vinyl)-3-cyano-4-(2-methyl-3-trifluoromethyl)-pyrrole or N-(1-diethylamino-2-methyl-vinyl)-3-cyano-4-(2,3,4-trichloro)-pyrrole.

* * * * *

UNITED STATES PATENT AND TRADEMARK OFFICE
CERTIFICATE OF CORRECTION

PATENT NO. : 5,061,312

DATED : October 29, 1991

INVENTOR(S) : Heinemann et al.

It is certified that error appears in the above-identified patent and that said Letters Patent is hereby corrected as shown below:

Title Page      ABSTRACT: Lines 13-14 delete " halogenaolakyl " and substitute -- halogenoalkyl --

Col. 13, lines 7-8      After " identical " insert -- or --

Signed and Sealed this

Sixth Day of July, 1993

Attest:

MICHAEL K. KIRK

*Attesting Officer*      Acting Commissioner of Patents and Trademarks